United States Patent [19]

Kuzmin

[11] 4,124,302

[45] Nov. 7, 1978

[54] DEVICE FOR PHOTOMETERING A SUBSTANCE PLACED IN A CYLINDER-SHAPED CELL

[75] Inventor: Sergei V. Kuzmin, Novosibirsk, U.S.S.R.

[73] Assignee: Novosibirsky Institut Organicheskoi Khimii Sibirskogo Otdelenia Akademii Nauk SSSR, Novosibirsk, U.S.S.R.

[21] Appl. No.: 775,854

[22] Filed: Mar. 9, 1977

[30] Foreign Application Priority Data

Mar. 11, 1976 [SU] U.S.S.R. .............................. 2337479

[51] Int. Cl.² .............................................. G01N 21/24
[52] U.S. Cl. .................................. 356/440; 250/573; 350/293
[58] Field of Search ............... 356/207, 208, 103, 180; 250/573, 343, 373; 350/293

[56] References Cited

U.S. PATENT DOCUMENTS

| 2,149,735 | 3/1939 | Henderson | 250/574 |
| 3,013,467 | 12/1961 | Minsky | 356/201 |
| 3,248,551 | 4/1966 | Frommer | 356/103 |
| 3,457,407 | 7/1969 | Goldberg | 356/103 |
| 3,508,809 | 4/1970 | Wilder et al. | 350/152 |

*Primary Examiner*—John K. Corbin
*Assistant Examiner*—R. A. Rosenberger
*Attorney, Agent, or Firm*—Lackenbach, Lilling & Siegel

[57] ABSTRACT

A device for photometering a substance placed in a cylindershaped cell, comprising an aperture diaphragm and an elliptical mirror successively arranged in the path of a light beam emitted by a light source. The elliptical mirror is installed coaxially to the cylinder-shaped cell containing the substance to be photometered. The light beam, incident on the eliptical mirror and reflected therefrom, is focused on said cell and then collected on a photoreceiver. In the path of the light beam, incident on the elliptical mirror and reflected from said mirror, is arranged a semi-transparant mirror is arranged for directing the light beam passing through said cell to the photoreceiver. The device has low sensitivity to axial displacement of the cell with respect to the optical axis thereof, and also exhibits low sensitivity to rotation of said cell about its axis.

2 Claims, 1 Drawing Figure

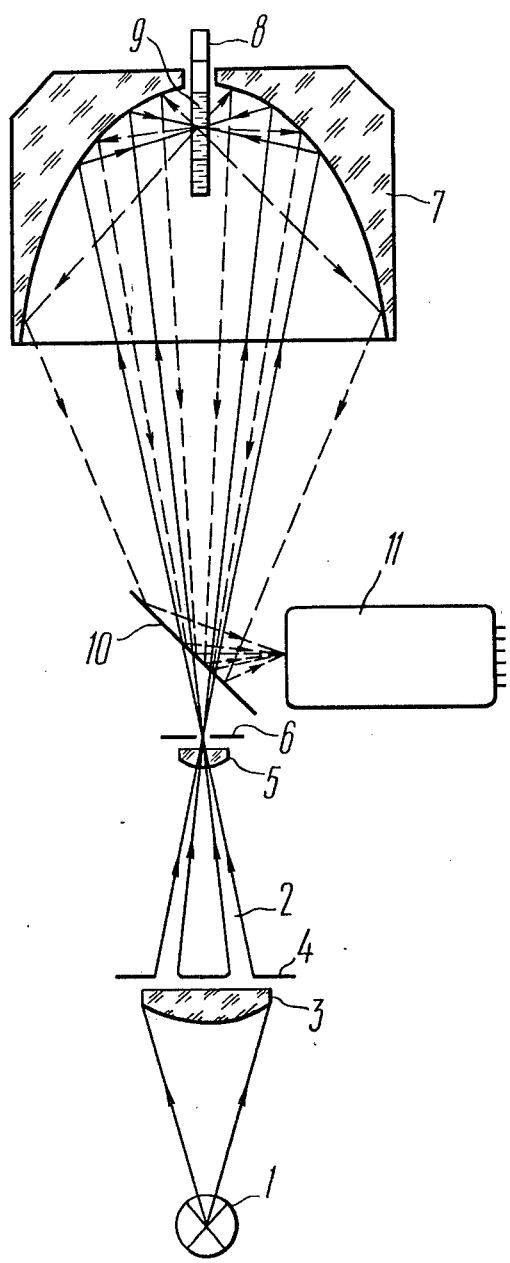

DEVICE FOR PHOTOMETERING A SUBSTANCE PLACED IN A CYLINDER-SHAPED CELL

The present invention relates to optical measuring devices, and, more particularly, to devices for photometering a substance placed in a cylinder-shaped cell, which can be advantageously used in medicine, biology and chemistry for qualitative and quantitative analysis of microquantities of substances.

At present, stringent accuracy requirements are imposed on devices for photometering substances placed in replaceable cylinder-shaped cells. This is due to the extremely high sensitivity of said devices, and to the accuracy of the positioning and geometry of the replaceable cells.

Known in the art are devices for photometering a substance placed in a cylinder-shaped cell, characterized in that the optical axis of a device is perpendicular to that of the cylinder-shaped cell.

Also known in the art is a device for photometering a substance placed in a cylinder-shaped cell, comprising a light source and an aperture diaphragm arranged in the path of a light beam emitted by said light source, said diaphragm being intended for limiting said light beam, which light beam is then focused on the cylinder-shaped cell containing the substance to be photometered, and passes through said cell, and is collected on a photoreceiver.

In said device, the light beam, limited by the aperture diaphragm, is focused by means of a condensor (lens) on the cylinder-shaped cell containing the substance to be photometered, which condensor is interposed in the path of the light beam past the aperture diaphragm. The light beam, which has passed through said cell, is then collected by a similar condensor interposed in the path of the light beam intermediate of said cell and the photoreceiver.

The above devices are extremely susceptible to the positioning and shape of the cylinder-shaped cell, which can change, e.g., when scanning or replacing the cell, thus affecting the reproducibility of the photometering results.

It is an object of the present invention to provide a device for photometering a substance placed in a cylinder-shaped cell, having low sensitivity to both the positioning and to any imperfection in the shape of said cell.

These and other objects of the invention are attained by providing a device for photometering a substance placed in a cylinder-shaped cell, comprising an aperture diaphragm arranged in the path of a light beam emitted by a light source for limiting same. The beam is focused on the cylinder-shaped cell containing the substance to be photometered, passes through said cell, and is collected on a photoreceiver. An elliptical mirror focuses the light beam which is incident thereon, on the cylinder-shaped cell containing the substance to be photometered, and also collects the light beam reflected from the elliptical mirror after said beam has passed through said cell. The mirror is positioned coaxially to said cell, and a semi-transparant mirror is arranged in the path of the light beam, incident on the elliptical mirror and reflected therefrom, for directing said light beam, which has passed through the cylinder-shaped cell, to the photoreceiver.

It is preferable that the aperture diaphragm should be annular so as to provide for axisymmetrical illumination of the cylinder-shaped cell containing the substance to be photometered, and prevent illumination of the end face of said cell and the portion of the elliptical mirror, proximal to said cell.

The proposed device for photometering a substance placed in a cylinder-shaped cell has low sensitivity to the axial displacement of said cell in respect to the optical axis of the device and is not sensitive to the rotation of said cell about its axis. Said device allows the use of cells very small in diameter (capillaries), which make it possible to analyze microquantities of substances.

The features and merits of the present invention will be more readily understood from a consideration of a detailed description of a preferred embodiment thereof to be read in conjunction with the accompanying drawing illustrating an optical diagram of a device for photometering a substance placed in y cylinder-shaped cell (a partial longitudinal section), according to the present invention.

The proposed device for photometering a substance placed in a cylinder-shaped cell comprises a light source 1, emitting a luminous flux which is shaped into a light beam 2 by means of a condensor which is a lens 3. In the path of the light beam 2, past the lens 3 and in immediate proximity thereto, an annular aperture diaphragm 4 is arranged for limiting the light beam 2.

In the path of the light beam 2, past aperture diaphragm a collective lens 5 is arranged, The aperture diaphragm 4 is ring-shaped and is located in the focus of the collective lens 5. In the path of the light beam 2 there is also arranged a field diaphragm 6 which is in the focus of the lens 3 and in one of the foci of an elliptical mirror 7 arranged further along the path of the light beam 2. In the second focus of the collective lens 5, the elliptical mirror 7 is arranged with its axis coaxial to a cylinder-shaped cell 8, containing a substance to be photometered 9. This substance absorbs light within the range of the working wave lengths. In the present embodiment, the substance is a liquid. The elliptical mirror 7 is intended for focusing the light beam 2, on the cylinder-shaped cell 8, and collecting said light beam 2, reflected from the elliptical mirror 7 after said beam 2 has passed through said cell 8. The aperture diaphragm 4 provides for axisymmetrical illumination of the cylinder-shaped cell 8 by the light beam 2, reflected from the elliptical mirror 7, and prevents the illumination of the end face of the cylinder-shaped cell 8 and the portion of the elliptical mirror 7 in immediate proximity to said cell 8. A semi-transparent mirror 10 for dividing said light beam 2 is interposed between the elliptical mirror 7 and the field diaphragm 6 in the path of the light beam which is incident on the eliptical mirror and reflected therefrom 7. The semi-transparant mirror 10, is positioned at an angle to the axis of the eliptical mirror 7, and directs the light beam 2 to the photoreceiver 11 which is arranged symmetrically to the field diaphragm 6 with respect to the semi-transparant mirror 10.

The proposed device operates as follows.

The luminous flux, emitted by the light source 1, is shaped by the condensor 3 and limited by the aperture diaphragm 4 into a light beam 2 which then passes through the collective lens 5, field diaphragm 6, and falls on the semi-transparant mirror 10. A portion of the light beam 2 is reflected from the semi-transparant mirror 10 and thus is of no further use. The portion of the light beam 2, which passes through the semi-transparant mirror 10, falls on the eliptical mirror 7, and is then focused on the cylinder-shaped cell 8 containing the substance 9 to be photometered. The light beam 2, which has passed through the cell 8, is partially absorbed by the substance 9 therein and falls on the elliptical mirror 7 where it is collected by said mirror 7 and partially reflected from the semi-transparant mirror 10, whereafter it falls on the photoreceiver 11. The photreceiver generates a signal proportional to the amount of light which has passed through the cylinder-shaped cell 8 containing the substance to be photometered 9, and the signal is registered by an electronic circuit (not shown). The cylinder-shaped cell 8 is simultaneously illuminated from all radial directions crossing the focus of the elliptical mirror 7 and limited by the action of the aperture diaphragm in the meridian planes.

The working solid angle of the elliptic mirror 7, at which the light is collected, after it has passed through the cylinder-shaped cell, can be 90 percent of the full solid angle, and, therefore, practically all the amount of light, which has passed through the cell 8, or has been reflected therefrom, is collected and directed to the photoreceiver 11. This helps to reduce the sensitivity of said device to light diffusion in the substance 9 placed in the cylinder-shaped cell 8.

The rotational symmetry of the illumination system, and, in particular, of the elliptical mirror 7, and its coaxial disposition with the cylinder-shaped cell 8 helps to reduce the light sensitivity of said device to the positioning and imperfection in the geometry or shape of the cell 8, and also fully eliminate a change in sensitivity of the device to light absorbtion of the substance 9 placed in the cylinder-shaped cell 8 with axial rotation of said cell 8.

What is claimed is:

1. A device for photometering a substance placed in a cylinder-shaped cell comprising: a light source; a light beam emitted by said light source; an aperture diaphragm arranged in the path of said light beam for limiting said light beam; an elliptical mirror arranged in the path of said light beam beyond said aperture diaphragm, and coaxially with said cylinder-shaped cell containing a substance to be photometered for focusing said light beam on said cell; and a photoreceiver, in the path of said light beam after said light beam has passed through said cell and has been collected by said elliptical mirror and thereafter reflected by a semi-transparent mirror, for producing a signal proportional to the amount of light passing through said cell.

2. A device as claimed in claim 1, wherein said aperture diaphragm is ring-shaped.

* * * * *